United States Patent
Kume et al.

(10) Patent No.: US 6,878,663 B2
(45) Date of Patent: Apr. 12, 2005

(54) METHOD FOR PRODUCING PALLADIUM COMPLEX COMPOUND

(75) Inventors: Takashi Kume, Saitama (JP); Satoru Narizuka, Saitama (JP); Makoto Koide, Saitama (JP); Koichi Mikami, Yokohama (JP); Manabu Hatano, Tokyo (JP); Masahiro Terada, Saitama (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 10/116,057

(22) Filed: Apr. 5, 2002

(65) Prior Publication Data

US 2002/0111482 A1 Aug. 15, 2002

Related U.S. Application Data

(62) Division of application No. 09/458,080, filed on Dec. 10, 1999.

(30) Foreign Application Priority Data

| Dec. 10, 1998 | (JP) | 10-351529 |
| Dec. 10, 1998 | (JP) | 10-351530 |
| Jun. 24, 1999 | (JP) | 11-178393 |
| Jun. 24, 1999 | (JP) | 11-178394 |
| Jun. 24, 1999 | (JP) | 11-178395 |
| Nov. 19, 1999 | (JP) | 11-329084 |

(51) Int. Cl.$^7$ .............................................. C07F 17/02
(52) U.S. Cl. ....................................... 502/155; 556/22
(58) Field of Search ............................ 502/155; 556/22

(56) References Cited

PUBLICATIONS

Tolman, C. A. Chem. Rev. 77(3) (1977) 313–348.*
Dierkes, P.; van Leeuwen W. N. M. J. Chem. Soc., Dalton Trans. (1999) 1519.*
Kravtsov, D. N.; Peregudov, A. S.; Drogunova, G. I. Russ. Chem. Bull. 46(3) (1997) 572–576.*
Yang, B. H.; Buchwald, S. L. J. Organomet. Chem. 576 (1999) 125–146.*
Herrmann, W. A.; BroBmer, C.; Priermeier, T.; Ofele, K. J Organomet. Chem. 481 (1994) 97–108.*
Ozawa, et al., (1991) "Catalytic Asymmetric Arylation of 2,3–Dihydrofuran with Aryl Triflates" *J. Am. Chem. Soc.* 113:1417–1419.

Sato et al., (1989) "Catalytic Asymmetric C—C Bond Formation: Asymmetric Synthesis of cis–Decalin Derivatives by Palladium–Catalyzed Cyclization of Prochiral Alkenyl Iodides" *J. Org. Chem.* 54:4738–4739.
Fitton et al., (1971) "The Addition of Aryl Halides to Tetrakis (triphenylphosphine) palladium (0)" *J. Organomet. Chem.* 28:287–291.
Wallow et al., (1996) "New Methods for the Synthesis of ArPdL$_2$I (L=Tertiary Phosphine) Complexes" *J. Organometallics* 15:3708–3716.
Vedernikov et al., (1994) "Reversible Thermal Carbon–Hydrogen Bond Cleavage in Alkanes and Arenes with Dihalogenobis (triphenylphosphine) palladium ($_{11}$) Complexes" *J. Chem. Commun.* 121–122.
Grushin et al., (1995) "Indirect Formation of Carboxylic Acids via Anhydrides in the Palladium–Catalyzed Hydroxycarbonylation of Aromatic Halides" *J. Am. Chem. Soc.* 117:4305–4315.
Meyer et al., (1998) "Thioethercarboxylates in palladium chemistry: First proof of hemilabile properties of S–O ligands" *J. Oraganomet. Chem.* 553:83–90.

* cited by examiner

*Primary Examiner*—V. Balasubramanian
(74) *Attorney, Agent, or Firm*—Crowell & Moring LLP

(57) ABSTRACT

An aromatic compound represented by the general formula Ar$^1$X is reacted with a palladium compound and a phosphine derivative, in the presence of a first basic substance, thereby producing a palladium-complex compound represented by the general formula Ar$^1$—PdL$_2$X. This palladium-complex compound is reacted with a benzoic acid represented by the general formula Ar$^2$—COOH, in the presence of a second basic substance, thereby producing another palladium-complex compound represented by the following general formula.

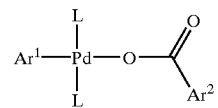

The above palladium-complex compounds are useful as catalysts and can be produced easily by the above reactions. In the above general formulas, Ar$^1$ is an aryl group; and X is a halogen that is fluorine, chlorine, bromine or iodine, trifluoromethanesulfonate group, an alkylsulfonate group having a carbon atom number of 1–4, or a substituted or unsubstituted arylsulfonate group; each L is independently a phosphine ligand; and Ar$^2$ is an aryl group.

27 Claims, No Drawings

METHOD FOR PRODUCING PALLADIUM COMPLEX COMPOUND

This application is a division of co-pending application Ser. No. 09/458,080, filed Dec. 10, 1999.

BACKGROUND OF THE INVENTION

The present invention relates to a method for producing a palladium-phosphine complex compound, which is useful as a catalyst of organic synthesis.

Hitherto, various transition metal complexes have been used as catalysts of organic synthesis. In particular, noble metal complexes are stable and easy to handle. Thus, they are widely used as catalysts for organic synthesis, although they are high in price. Of optically active ligands of transition metal complexes used in asymmetric catalytic reactions, a ligand of 2,2'-bis(diphenylphosphino)-1,1'-binaphtyl (hereinafter referred to as "BINAP") is one of the most superior ligands in asymmetry differentiation capability. It has been reported in J. Am. Chem. Soc., 1991, Vol. 118, pp. 1417 and J. Org. Chem., 1989, Vol. 54, pp. 4738 that a palladium complex having a ligand of BINAP is very much superior in catalytic activity, particularly in enantio-selectivity, for Heck reaction to an olefin, which is an asymmetric carbon-carbon bond formation reaction. In such reaction, there is assumed an involvement of an intermediate of [PhPd(I)(BINAP)], which is formed by an oxidative addition of benzene iodide to Pd(0)-BINAP formed in the reaction system.

There are known palladium complex compounds having ligands of trifluoromethylphenyl and tris(trifluoromethyl)phenyl, which are represented by the general formulas:

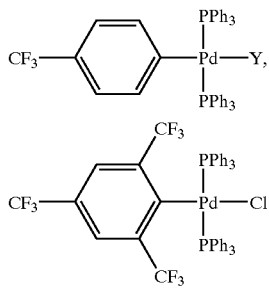

where Y is fluorine, chlorine, bromine, or iodine.

J. Organomet. Chem., 1971, 28, 287 discloses a method for producing a palladium complex compound represented by the general formula $Ar^1Pd(PPh_3)_2X^1$ where $Ar^1$ represents an aryl and $X^1$ is a halogen. In this method, a stable palladium complex $Pd^0(PPh_3)_4$ is reacted with an aryl halide. J. Organometallics, 1996, 15(17), 3708 discloses a similar method in which a palladium complex $Pd_2(dba)_3$ is used.

J. Chem. Commun., 1994, 121 discloses a reaction of dibromobis(triphenylphosphine)palladium(II) with toluene in the presence of potassium carbonate at 130° C. for 1 hr to obtain a small amount of bromo [methylphenyl]bis(triphenylphosphine)palladium(II).

J. Am. Chem. Soc., Vol. 117, No. 15, 4305 (1995) discloses a method for producing a palladium complex compound having a benzoato ligand, represented by the formula $(Ph_3P)_2PdPh(PhCOO)$. In this method, $(Ph_3P)_2Pd_2Ph_2(\mu{-}OH)_2$ is dispersed in benzene. Then, benzoic acid is added to the mixture to have a solution having a pale yellow color. Then, the solvent is distilled away. After that, n-hexane is added, thereby obtaining $(Ph_3P)_2Pd_2Ph_2(\mu{-}PhCOO)_2$ in the form of crystal. The obtained crystals are dispersed in benzene. Then, triphenylphosphine is added, thereby preparing a transparent solution. Then, the solvent is distilled away. After that, n-hexane is added, thereby obtaining the aimed palladium complex compound in the form of crystal.

J. Oraganomet. Chem. 553 (1998) 83–90 discloses a method for producing trans-[Pd(OOC—($C_6H_4$)-2—SMe—$\kappa^1$—O)Ph(PPh$_3$)$_2$]. In this method, a thallium salt 2-RS—$C_6H_4$—COOTl is prepared by reacting 2—RS—$C_6H_4$—COOH with thallium carbonate in ethanol. Then, the thallium salt is reacted with trans-[PdCl(Ph)(PPh$_3$)$_2$] in tetrahydrofuran, thereby obtaining the product with a precipitate of thallium chloride.

SUMMARY OF THE INVENTION

It is an object of the present invention to provide a method for easily producing a palladium complex compound that is useful as catalyst.

It is another object of the present invention to provide a palladium complex compound that is superior in physical and/or chemical properties.

According to a first aspect of the present invention, there is provided a first method for producing a first palladium-complex compound represented by the general formula (4). With this, it is possible to easily obtain the product by the following reaction steps (a) and (b). The first method comprises:

(a) reacting an aromatic compound represented by the general formula (1), with a palladium compound and a phosphine derivative, in the presence of a first basic substance, thereby obtaining a second palladium-complex compound represented by the general formula (2); and (b) reacting said second palladium-complex compound with a benzoic acid represented by the general formula (3), in the presence of a second basic substance, thereby producing said first palladium-complex compound, $$Ar^1X \tag{1}$$

where $Ar^1$ is an aryl group; and X is a halogen that is fluorine, chlorine, bromine or iodine, trifluoromethanesulfonate group, an alkylsulfonate group having a carbon atom number of 1–4, or a substituted or unsubstituted arylsulfonate group, $$Ar^1{-}PdL_2X \tag{2}$$

where each L is independently a phosphine ligand, and $Ar^1$ and X are defined as above, $$Ar^2{-}COOH \tag{3}$$

where $Ar^2$ is an aryl group,

where $Ar^1$, $Ar^2$, and L are defined as above.

According to a second aspect of the invention, there is provided a second method for producing the second palladium-complex compound represented by the general formula (2). With this, it becomes possible to easily obtain the product, using stable chemical substances that are easily obtainable. The second method comprises the reaction step (a) of the first method, thereby obtaining the second palladium-complex compound.

According to a third aspect of the invention, there is provided a third method for producing the first palladium-complex compound represented by the general formula (4). The third method comprises reacting a second palladium-complex compound represented by the general formula (2), with a benzoic acid represented by the general formula (3), in the presence of a basic substance, thereby producing the first palladium-complex compound.

According to a fourth aspect of the invention, there is provided a fourth method for producing the first palladium-complex compound represented by the general formula (4). As compared with the first method, the fourth method comprises a single reaction step of reacting an aromatic compound represented by the general formula (1), with a palladium compound, a phosphine derivative and a benzoic acid derivative represented by the general formula (3), in the presence of a basic substance, thereby obtaining the first palladium-complex compound.

According to a fifth aspect of the invention, there is provided a novel palladium complex compound. This compound, which can be produced by the above-mentioned first, third or fourth method, is represented by the general formula (5),

(5)

where $Ar^3$ and $Ar^4$ are respectively aryl groups represented by the general formulas (6) and (7), and each L is independently a phosphine ligand,

(6)

where $R^2$ is trifluoromethyl group, trifluoromethyloxy group, a halogen that is fluorine, chlorine, bromine or iodine, nitro group, acetyl group, cyano group, an alkyl group having a carbon atom number of 1–4, an alkoxyl group having a carbon atom number of 1–4, or an aloxycarbonyl group having a carbon atom number of 2–5; and m is an integer of 0–4,

(7)

where $R^1$ is trifluoromethyl group, and n is an integer of 1–3.

According to a sixth aspect of the invention, there is provided a novel palladium complex compound. This compound, which can be produced by the above-mentioned second method, is represented by the general formula $Ar^5$—$PdL_2X$ where $Ar^5$ is bis(trifluoromethyl)phenyl group, X is a halogen that is fluorine, chlorine, bromine or iodine, and each L is independently a phosphine ligand.

DESCRIPTION OF THE PREFERRED EMBODIMENTS

The above-mentioned first to fourth methods according to the invention will be described in detail, as follows.

In the aromatic compound $Ar^1X$ used in the first, second and fourth methods and the second palladium-complex compound $Ar^1$—$PdL_2X$ used in the third method, X is defined as above and preferably bromine or iodine in practical use.

In the aromatic compound $Ar^1X$ used in the first, second and fourth methods and the second palladium-complex compound $Ar^1$—$PdL_2X$ used in the third method, $Ar^1$ is defined as being an aryl group, as mentioned above. This aryl group $Ar^1$ can be selected from carbon cyclic groups, such as phenyl and naphthyl, and heterocyclic groups, such as pyridyl and quinolyl. These groups may have substituents. The aryl group $Ar^1$ is preferably one represented by the general formula (6),

(6)

where $R^2$ is a halogen that is fluorine, chlorine, bromine or iodine, or a monovalent organic group, and m is an integer of 0–4. The substituent $R^2$ is not particularly limited so long as it is inert in the reaction of the invention.

In the benzoic acid $Ar^2$—COOH used in the first, third and fourth methods, $Ar^2$ is also defined as being an aryl group, as mentioned above. This aryl group $Ar^2$ can also be selected from the above-mentioned exemplary groups of the aryl group $Ar^1$. The exemplary groups of the aryl group $Ar^2$ may also have substituents. The aryl group $Ar^2$ is preferably one represented by the general formula (7),

(7)

where $R^1$ is defined as $R^2$ of the general formula (6) and n is an integer of 0–3. The substituent $R^1$ is not particularly limited so long as it is inert in the reaction of the invention.

Examples of the substituents $R^1$ and $R^2$ in the general formulas (6) and (7) are trifluoromethyl group, trifluoromethyloxy group, halogens that are fluorine, chlorine, bromine and iodine, nitro group, acetyl group, cyano group, alkyl groups each having a carbon atom number of 1–4, alkoxyl groups each having a carbon atom number of 1–4, and alkoxycarbonyl groups each having a carbon atom number of 2–5. Examples of the alkyl group are methyl group, ethyl group, n-propyl group, and i-propyl group. Examples of the alkoxyl group are methoxy group, ethoxy group, n-propoxy group, and i-propoxy group. Examples of the alkoxycarbonyl group are methoxycarbonyl group, ethoxycarbonyl group, n-propoxycarbonyl group, and i-propoxycarbonyl group. The aryls group $Ar^1$ is preferably one in which at least one of $R^2$ is trifluoromethyl group. The aryl group $Ar^2$ is also preferably one in which at least one of $R^1$ is trifluoromethyl group.

Examples of the aryl groups $Ar^1$ and $Ar^2$ used in the first to fourth methods are (1) aryl groups each having one trifluoromethyl, such as 2-trifluoromethylphenyl, 3-trifluoromethylphenyl, and 4-trifluoromethylphenyl, (2) aryl groups each having one trifluoromethoxy, such as 2-trifluoromethoxyphenyl, 3-trifluoromethoxyphenyl, and 4-trifluoromethoxyphenyl, (3) aryl groups each having one fluorine, such as 2-fluorophenyl, 3-fluorophenyl, and 4-fluorophenyl, (4) aryl groups each having one chlorine, such as 2-chlorophenyl, 3-chlorophenyl, and 4-chlorophenyl, (5) aryl groups each having one bromine, such as 2-bromorophenyl, 3-bromorophenyl, and 4-bromorophenyl, (6) aryl groups each having one iodine, such as 2-iodophenyl, 3-iodophenyl, and 4-iodophenyl, (7) aryl groups each having one nitro group, such as 2-nitrophenyl, 3-nitrophenyl, and 4-nitrophenyl, (8) aryl groups each having one acetyl, such as 2-acetylphenyl, 3-acetylphenyl, and 4-acetylphenyl, (9) aryl groups each having one cyano group, such as 2-cyanophenyl, 3-cyanophenyl, and 4-cyanophenyl, (11) aryl groups each having one alkyl, such as 2-methylphenyl, 3-methylphenyl, 4-methylphenyl, 2-ethylphenyl, 3-ethylphenyl, and 4-ethylphenyl, (12) aryl groups each having one alkoxy, such as 2-methoxyphenyl, 3-methoxyphenyl, 4-methoxyphenyl, 2-ethoxyphenyl, 3-ethoxyphenyl, and 4-ethoxyphenyl, and (13) aryl groups each having one alkoxycarbonyl, such as 2-methoxycarbonylphenyl, 3-methoxycarbonylphenyl, 4-methoxycarbonylphenyl, 2-ethoxycarbonylphenyl, 3-ethoxycarbonylphenyl, and 4-ethoxycarbonylphenyl. Each of the aryl groups $Ar^1$ and $Ar^2$ may have at least two substituents. These at least two substituents may be any arbitrary combination of various substituents. One of the at least two substituents of the aryl group $Ar^1$ or $Ar^2$ is preferably trifluoromethyl group. Nonlimitative examples of such aryl groups $Ar^1$ and $Ar^2$ are 2-chloro-3-(trifluoromethyl)phenyl, 2-fluoro-3-(trifluoromethyl)phenyl, 2-fluoro-4-(trifluoromethyl)phenyl, 3-fluoro-5-(trifluoromethyl)phenyl, 2-bromo-6-(trifluoromethyl)phenyl, 4-chloro-2-(trifluoromethyl) phenyl, 4-fluoro-2-trifluoromethyl)phenyl, 2-chloro-6-(trifluoromethyl)phenyl, 4-fluoro-3-(trifluoromethyl)phenyl, 1-chloro 4-(trifluoromethyl)phenyl, 2-fluoro-6-(trifluoromethyl)phenyl, 2-fluoro-5(trifluoromethyl)phenyl, 2-chloro-4-(trifluoromethyl)phenyl, 4-chloro-3-(trifluoromethyl)phenyl, 4-chloro-2-(trifluoromethyl)phenyl and the like; 2-methyl-3-(trifluoromethyl)phenyl, 3-methyl-5-(trifluoromethyl)phenyl, 2-methyl-4-(trifluoromethyl) phenyl, 4,5-dimethyl-2-(trifluoromethyl)phenyl, 2-methyl-5-(trifluoromethyl)phenyl, 5,6-dimethyl-2-(trifluoromethyl) phenyl, 4-methyl-3-(trifluoromethyl)phenyl, and the like; 2-methoxy-4-(trifluoromethyl)phenyl, 2-ethoxy-4-(trifluoromethyl)phenyl, 4-ethoxy-2-(trifluoromethyl) phenyl, 4-methoxy-2-(trifluoromethyl)phenyl, 2-methoxy-5-(trifluoromethyl)phenyl, and the like; 2-nitro-3-(trifluoromethyl)phenyl, 2-nitro-4-(trifluoromethyl)phenyl, 4-nitro-2-(trifluoromethyl)phenyl, 3-nitro-5-(trifluoromethyl)phenyl, 2-nitro-5-(trifluoromethyl)phenyl, 4-nitro-3-(trifluoromethyl)phenyl, and the like; 2-cyano-5-(trifluoromethyl)phenyl, 2-cyano-4-(trifluoromethyl)phenyl, 4-fluoro-3-cyano-5-(trifluoromethyl)phenyl, 4-cyano-3-(trifluoromethyl)phenyl, 2-chloro-5-cyano-3-(trifluoromethyl)phenyl, 4-cyano-2-(trifluoromethyl)phenyl, and the like; and 2-amino-6-(trifluoromethyl)phenyl, 2-amino-5-(trifluoromethyl)phenyl, 2-amino-4-(trifluoromethyl)phenyl, 2-amino-3-(trifluoromethyl) phenyl, 3-amino-6-(trifluoromethyl)phenyl, 3-amino-5-(trifluoromethyl)phenyl, 4-amino-2-(trifluoromethyl) phenyl, 4-amino-3-(trifluoromethyl)phenyl, and the like. Each aryl group $Ar^1$ or $Ar^2$ is preferably one having at least two trifluoromethyl groups. Examples of such aryl group are 2,3-bis(trifluoromethyl)phenyl, 2,4-bis(trifluoromethyl) phenyl, 2,5-bis(trifluoromethyl)phenyl, 2,6-bis (trifluoromethyl)phenyl, 3,4-bis(trifluoromethyl)phenyl, and 3,5-bis(trifluoromethyl)phenyl. Further nonlimitative examples of such aryl group are 2,3,4-tris(trifluoromethyl) phenyl 2,4,5-tris(trifluoroethyl)phenyl, 2,3,5-tris (trifluoromethyl)phenyl, 1,3,5-tris(trifluoromethyl)phenyl, 3,4,5-tris(trifluoromethyl)phenyl, 2,3,4,6-tetrakis (trifluoromethyl)phenyl, 1-bromo-2,3,4-tris (trifluoromethyl)phenyl, 2-bromo-4,5,6-tris (trifluoromethylphenyl, and the like; and 3,5-dichloro-4,6-bis(trifluoromethyl)phenyl, 2-dichloro-3,5-bis (trifluoromethyl)phenyl, 2-methoxy-3,5-bis (trifluoromethyl)phenyl, 2-bromo-3,5-bis(trifluoromethyl) phenyl, 2-nitro-4,6-bis(trifluoromethyl)phenyl, 5,6-dichloro-1,3-bis(trifluoromethyl)phenyl, 4-chloro-3,5-bis (trifluoromethyl)phenyl, and the like.

The second palladium-complex compound ($Ar^1$—$PdL_2X$), which is used in the third method of the invention, is preferably one in which at least one of $R^2$ is trifluoromethyl group and more preferably one in which at least two of $R^2$ are trifluoromethyl groups, since the aimed product becomes extremely useful. The benzoic acid ($Ar^2$—COOH), which is used in the first, third and fourth methods of the invention, is preferably one in which at least one of $R^1$ is trifluoromethyl group and more preferably one in which at least two of $R^1$ are trifluoromethyl groups, since the aimed product becomes extremely useful.

As stated above, the starting material of the third method is the second palladium-complex compound represented by the general formula (2), $Ar^1$—$PdL^2X$, where each L is independently a phosphine ligand. Furthermore, the phosphine derivative is used in the first, second and fourth methods. Such phosphine (phosphine derivative or phosphine ligand) used in the first to fourth methods is not particularly limited and may be one represented by the general formula $P(R^1)_3$, which can be a monodentate ligand in $Ar^{1—PdL}{}_2X$, where each $R^1$ is independently a first group selected from the group consisting of lower alkyl groups, cycloalkyl groups, phenyl group, naphthyl group, arthryl group, pyridyl group and quinolyl group. The first group optionally has a first substituent $R^2$ selected from the group consisting of nitro group, primary amino group, secondary amino group, tertiary amino group, halogen atoms, and a second substituent. The second substituent is selected from the group consisting of lower alkyl groups, cycloalkyl groups, phenyl group, naphthyl group, anthryl group, pyridyl group and quinolyl group. The second substituent optionally has a third substituent $R^3$ selected from the group consisting of nitro group, primary amino group, secondary amino group, tertiary amino group, halogen atoms, and a substituent being selected from the group consisting of lower alkyl groups, lower alkoxy groups, cycloalkyl groups, phenyl group, naphthyl group, anthryl group, pyridyl group, and quinolyl group. The substituent optionally has a substituent. In the present application, "lower alkyl groups", for example, of the above-mentioned phosphine, can be straight chain or branched alkyl groups each having a carbon atom number of 1–6. Examples of such lower alkyl groups are methyl group (hereinafter may be referred to as "Me"), ethyl group, n-propyl group, i-propyl group, n-butyl group, sec-butyl group, tert-butyl group, n-pentyl group, and n-hexyl group. In the present application, "lower alkoxy groups", for example, of the above-mentioned phosphine can be straight chain or branched alkoxy groups each having a carbon atom number of 1–6. Examples of such lower alkoxy groups are methoxy group (hereinafter may be referred to as "MeO"), ethoxy group, n-propoxy group, i-propoxy group, n-butoxy group, sec-butoxy group, tert-butoxy group, n-pentoxy group, and n-hexyloxy group.

In the above-mentioned phosphine represented by the general formula $P(R^1)_3$, at least one of $R^1$ is preferably phenyl group, o-tolyl group, m-tolyl group, p-tolyl group, 4-acynyl group, or 3,5-xylyl group. Concrete examples of such phosphine are triphenylphosphine, tris(o-tolyl)phosphine, tris(m-tolyl)phosphine, tris(p-tolyl)phosphine, tris(4-acynyl)phosphine, tris(3,5-xylyl)phosphine, and tris(n-butyl)phosphine. Of these, triphenylphosphine is particularly preferable. The phosphine $P(R^1)_3$ can be a first one represented by the following formula:

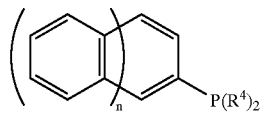

where n is an integer of 1–2, an arbitrary number of hydrogen atoms of the condensed ring may be replaced with the above-defined first substituent $R^2$, and each $R^4$ is independently phenyl group, o-tolyl group, m-tolyl group, p-tolyl group, 4-acynyl group, or 3,5-xylyl group. Such phosphine $P(R^1)_3$ can be a second one represented by the following formula:

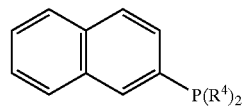

where an arbitrary number of hydrogen atoms of the naphthalene ring may be replaced with the above-defined first substituent $R^2$, and each $R^4$ is defined as above. Furthermore, the phosphine $P(R^1)_3$ can be a third one represented by the following formula:

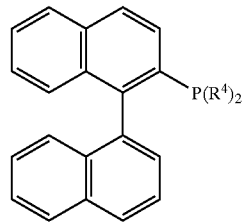

where an arbitrary number of hydrogen atoms of the naphthalene ring may be replaced with lower alkyl groups or lower alkoxy groups, and each $R^4$ is defined as above. Furthermore, the phosphine $P(R^1)_3$ can be a fourth one represented by the following formula:

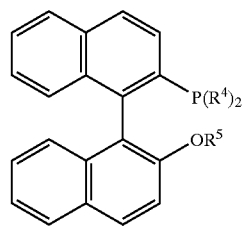

where $R^5$ is a lower alkyl group, and each $R^4$ is defined as above. Furthermore, the phosphine $P(R^1)_3$ can be fifth one represented by the following formula:

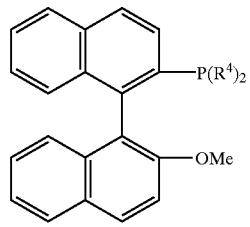

where each $R^4$ is defined as above. A preferable example of the second palladium-complex compound containing the above fifth phosphine, which can be used as the starting material of the third method, is one represented by the following formula:

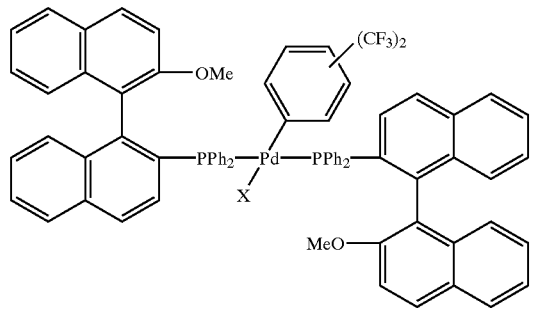

where X is a halogen that is fluorine, chlorine, bromine or iodine, trifluoromethanesulfonate group, an alkylsulfonate group having a carbon atom number of 1–4, or a substituted or unsubstituted arylsulfonate group. In this second palladium-complex compound, X is preferably bromine, and two of the trifluoromethyl group are particularly preferably bonded to the 3- and 5-positions.

The phosphine (i.e., phosphine derivative or phosphine ligand) used in the first to fourth methods maybe one represented by the general formula $(R^1)_2P—Q—P(R^1)_2$, which can be a bidentate ligand in $Ar^1—PdL_2X$, where each $R^1$ is defined as in the phosphine $P(R^1)_3$, and Q is a bivalent group. In the phosphine $(R^1)_2P—Q—P(R^1)_2$, at least one of $R^1$ is preferably phenyl group, o-tolyl group, m-tolyl group, p-tolyl group, 4-acynyl group, or 3,5-xylyl group. The bivalent group Q may comprise (1) an arbitrary number of a first bivalent group selected from alkylene group, phenylene group, naphthylene group, and anthrylene group, and (2) an arbitrary number of a bonding group selected from the group consisting of single bond, —O—, —S—, —C(=O)—, and —S(=O)—. The first bivalent group optionally has an arbitrary number of a substituent that can be selected from nitro group, primary amino group, secondary amino group, tertiary amino group, halogen atoms, lower alkyl groups, lower alkoxy groups, cycloalkyl groups, phenyl group, naphthyl group, anthryl group, pyridyl group, and quinolyl group. The bivalent group Q can be a preferable one selected from alkylene group, biphenylene group, binaphthylene group and bianthrylene group. This preferable one optionally has an arbitrary number of a group selected from nitro group, primary amino group, secondary amino group, tertiary amino group, halogen atoms, lower alkyl groups, lower alkoxy groups, cycloalkyl groups, phenyl group, naphthyl group, anthryl group, pyridyl group, and quinolyl group. The phosphine $(R^1)_2P—Q—P(R^1)_2$ can be a first one represented by the following general formula:

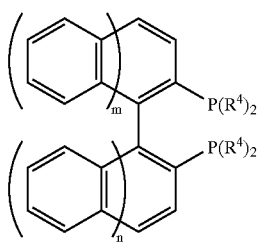

where an arbitrary number of hydrogen atoms of each aromatic ring may be replaced with the above-defined first substituent $R^2$, $R^4$ is defined as in the first one of the phosphine $P(R^1)_3$, each of m and n is independently an integer of 0–2. Furthermore, the phosphine $(R^1)_2P$—Q—P$(R^1)_2$ can be a second one represented by the following general formula:

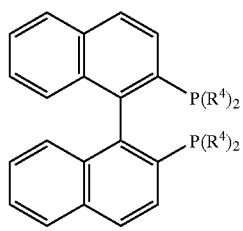

where an arbitrary number of hydrogen atoms of each aromatic ring may be replaced with the above-defined first substituent $R^2$, and $R^4$ is defined as in the first one of the phosphine $P(R^1)_3$. Furthermore, the phosphine $(R^1)_2P$—Q—P$(R^1)_2$ can be a third one represented by the following general formula:

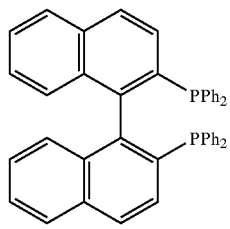

where an arbitrary number of hydrogen atoms of each aromatic ring may be replaced with a lower alkyl group or a lower alkoxy group. A preferable example of the second palladium-complex compound containing the above third phosphine $(R^1)_2P$—Q—P$(R^1)_2$, which can be used as the starting material of the third method, is one represented by the following formula:

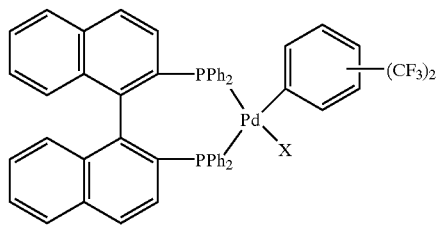

where X is a halogen that is fluorine, chlorine, bromine or iodine, trifluoromethanesulfonate group, an alkylsulfonate group having a carbon atom number of 1–4, or a substituted or unsubstituted arylsulfonate group. In this second palladium-complex compound, X is preferably bromine, and two of the trifluoromethyl group are particularly preferably bonded to the 3- and 5-positions.

The phosphine (i.e., the phosphine derivative or phosphine ligand) may be one represented by the general formula $(R^4)_2P$—$(CH_2)_q$—$P(R^4)_2$ where $R^4$ is defined as above, and q is an integer of 2–8. Furthermore, the phosphine may be one represented by the general formula $Ph_2P$—$(CH_2)_q$—$PPh_2$ where q is an integer of 2–8.

The palladium compound, which is used in the first, second and fourth methods, is preferably a palladium salt, such as palladium acetate, palladium chloride, palladium bromide, palladium iodide, or palladium nitrate. Furthermore, the palladium compound can be a palladium-complex(II), such as $[Pd(NH_3)_4]Y_2$, $Pd(NH_3)_2Y_2$, $Pd(NH_3)_4$, or $PdY_4$, where Y is halogen that is chlorine, bromine or iodine.

The basic substance, which is used in the first to fourth methods, including each of the first and second basic substances used in the first method, is not limited to a particular type. Nonlimitative examples of the basic substance are (1) ammonia and the like, such as ammonia and hydroxyamine, (2) amines, such as primary amine, secondary amine, tertiary amine, alicyclic amine (e.g., cyclopropylamine), and aromatic amine, and (3) inorganic bases, such as acetate (e.g., sodium acetate and potassium acetate), sodium hydroxide, potassium hydroxide, sodium carbonate, and potassium carbonate. Examples of the primary amine are propylamine, isopropylamine, butylamine, amylamine, and hexylamine. Examples of the secondary amine are diethylamine, dipropylamine, diisopropylamine, and dibutylamine. Examples of the third amine are triethylamine, tripropylamine, and tributylamine. Examples of the aromatic amine are triarylamine, N,N-dimethylaniline, N,N-diethylaniline, pyridine, and N-methylmorpholine.

It is optional to use a solvent in the first to fourth methods of the invention. Examples of such solvent are (1) aliphatic hydrocarbons, such as pentane, hexane, heptane, and octane, (2) aromatic hydrocarbons, such as benzene, toluene, and xylene, (3) ethers, such as diethyl ether, dioxane, tetrahydrofuran (THF), and ethylene glycol dimethyl ether, (4) ketones, such as acetone, methyl ethyl ketone, and methyl isobutyl ketone, (5) nitriles such as acetonitrile, (6) tertiary amines such as pyridine, (7) acid amides, such as N,N-dimethylformamide (DMF) and N,N-dimethylacetamide (DMAc), (8) sulfur-containing compounds, such as dimethylsulfoxide (DMSO) and sulforane, and (9) water. In case that a water-soluble basic substance is used in the reaction, it is preferable to use water, optionally together with one other solvent. Furthermore, the aromatic compound $Ar^1X$ itself, which is used in the first, second and fourth methods, can be used as a reaction solvent.

According to each of the second and fourth methods of the invention, it is essentially possible to complete the reaction in a single reaction vessel. Therefore, it becomes possible to remarkably simplify the reaction procedures. It is optional to modify the reaction of the second or fourth method by providing several reaction steps. Such modification is included in the scope of the invention.

In the first to fourth methods of the invention, the respective amounts of the raw materials used in the reaction are not particularly limited. In fact, it is preferable to use at least one mole of the aromatic compound $Ar^1X$ and at least two moles of the phosphine derivative, relative to 1 mol of palladium of the palladium compound, in the second method or the reaction step (a) of the first method. Furthermore, it is preferable to use at least one mole of the benzoic acid $Ar^2$—COOH, relative to one mol of palladium of the second palladium-complex compound $Ar^1$—$PdL_2X$, in the third method or the reaction step (b) of the first method. Similarly, it is preferable to use at least one mole of the aromatic compound $Ar^1X$, at least one mole of the benzoic acid $Ar^2$—COOH, and at least two moles of the phosphine derivative, relative to 1 mol of palladium of the palladium compound, in the fourth method. In the first to fourth methods, the respective amounts of the other raw materials, such as the basic substance and the solvent, are not particularly limited, and they can be used in respective suitable amounts.

The reaction in each of the first to fourth methods may be conducted as follows, and the following manner can be modified suitably. At first, a reaction vessel is charged with the raw materials (for example, in the case of the second method, the aromatic compound $Ar^1X$, the palladium compound, the phosphine derivative, the basic substance, and optionally solvent). The reaction vessel may or may not be pressurized and may or may not be stirred. The charged raw materials may or may not be heated to conduct the reaction, and the reaction may be conducted at a temperature of about 0–200° C., preferably of about 50–150° C. to accelerate the reaction. After the reaction, the reaction vessel may be cooled down, and then the contents of the reaction vessel are taken out. Then, an extraction solvent may be added to the contents, thereby separating solid matter. After that, volatile substances are distilled off from the filtrate, thereby obtaining the aimed product (e.g., the second palladium-complex compound in the case of the second method). If necessary, the aimed product can be purified through recrystallization, silica gel chromatography, or the like.

It should be noted that the second palladium complex compound $Ar_1$—$PdL_2X$ used in the third method is not limited to the reaction product of the second method or the reaction step (a) of the first method and may be prepared by a conventional method, as disclosed in J. Organomet. Chem., 1971, 28, 287, Organometallics, 1996, 15(17), 3708, and J. Chem. Commun., 1994, 121.

The above-stated novel first and second palladium complex compounds according to the fifth and sixth aspects of the invention will be described in detail, as follows. The first palladium complex compound, which can be produced by the first, third or fourth method, is represented by the general formula (5):

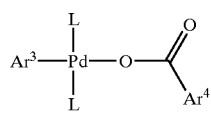

(5)

where $Ar^3$ and $Ar^4$ are respectively aryl groups represented by the above general formulas (6) and (7), and each L is independently a phosphine ligand. In the general formula (6) representing $Ar^3$, $R^2$ is trifluoromethyl group, trifluoromethyloxy group, a halogen that is fluorine, chlorine, bromine or iodine, nitro group, acetyl group, cyano group, an alkyl group having a carbon atom number of 1–4, an alkoxyl group having a carbon atom number of 1–4, or an alkoxycarbonyl group having a carbon atom number of 2–5. Examples of these alkyl group, alkoxy group and alkoxycarbonyl groups of $Ar^3$ are the same as the above-stated examples of those groups of $Ar^1$. In the general formula (7) representing $Ar^4$, $R^1$ is trifluoromethyl group. Examples of the aryl group $Ar^4$ are (1) aryl groups each having one trifluoromethyl, such as 2-trifluoromethylphenyl, 3-trifluoromethylphenyl, and 4-trifluoromethylphenyl, and (2) aryl groups each having two trifluoromethyl groups, such as 2,3-bis(trifluoromethyl)phenyl, 2,4-bis(trifluoromethyl)phenyl, 2,5-bis(trifluoromethyl)phenyl, 2,6-bis(trifluoromethyl)phenyl, 3,4-bis(trifluoromethyl)phenyl, and 3,5-bis(trifluoromethyl)phenyl. Of these, an aryl group having two trifluoromethyl groups is preferable, and 3,5-bis(trifluoromethyl)phenyl is more preferable. Thus, the palladium complex compound represented by the general formula (5) is preferably one represented by the following general formula:

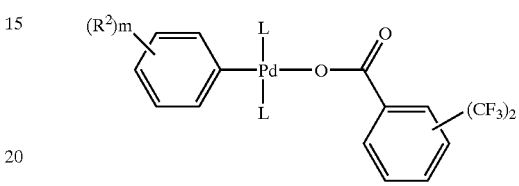

where $R^2$, m and L are defined as above in accordance with the fifth aspect of the invention. Furthermore, it is more preferably one represented by the following general formula:

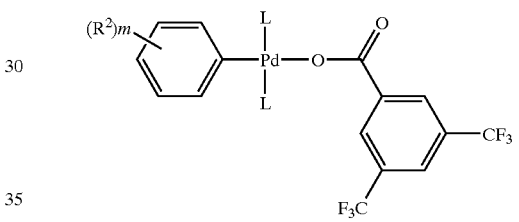

where $R^2$, m and L are defined as above in accordance with the fifth aspect of the invention. Similar to the aryl groups $Ar^1$ and $Ar^2$, the aryl group $Ar^3$ is preferably one in which at least one of $R^2$ is trifluoromethyl group. Examples of the aryl group $Ar^3$ are the same as those of the aryl groups $Ar^1$ and $Ar^2$. The aryl group $Ar^3$ may have at least two substituents. These at least two substituents may be any arbitrary combination of various substituents. One of the at least two substituents of the aryl group $Ar^3$ is preferably trifluoromethyl group. Nonlimitative examples of such aryl group $Ar^3$ are the same as those of the aryl groups $Ar^1$ and $Ar^2$. The aryl group $Ar^3$ is preferably one having at least two trifluoromethyl groups. Examples of such aryl group are the same as those of the aryl group $Ar^1$ or $Ar^2$. Further nonlimitative examples of the aryl group $Ar^3$ are the same as those of the aryl group $Ar^1$ or $Ar^2$.

As stated above, the second palladium complex compound according to the sixth aspect of the invention, which can be produced by the second method, is represented by the general formula $Ar^5$—$PdL_2X$ where $Ar^5$ is bis(trifluoromethyl)phenyl group, X is a halogen that is fluorine, chlorine, bromine or iodine, and each L is independently a phosphine ligand. Examples of the aryl group $Ar^5$ are 2,3-bis(trifluoromethyl)phenyl, 2,4-bis(trifluoromethyl)phenyl, 2,5-bis(trifluoromethyl)phenyl, 2,6-bis(trifluoromethyl)phenyl, 3,4-bis(trifluoromethyl)phenyl, and 3,5-bis(trifluoromethyl)phenyl. Of these, 3,5-bis(trifluoromethyl)phenyl is more preferable. The second palladium complex compound may be represented by the following general formula:

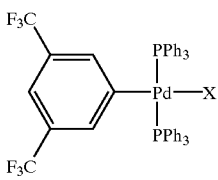

where Ph is phenyl group, and X is a halogen that is fluorine, chlorine, bromine or iodine. Preferable examples of the second palladium complex compound are those represented by the following general formulas:

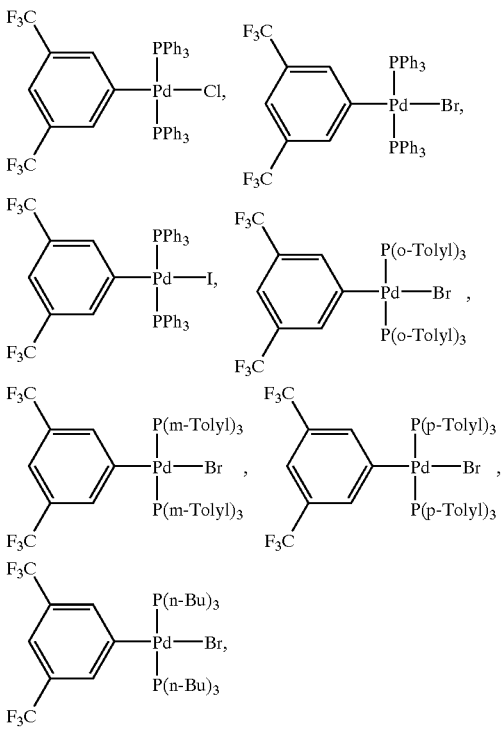

where Ph is phenyl group, Tolyl is tolyl group, and n-Bu is n-butyl group. Of these, more preferable examples are those represented by the following formulas.

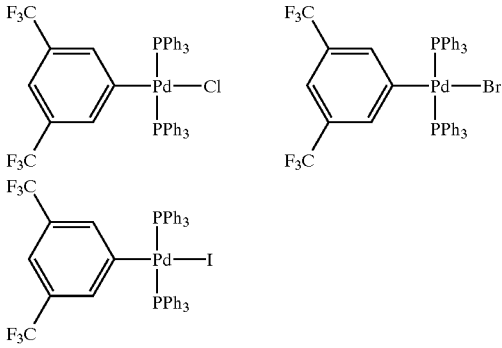

The phosphine ligand of each of the novel first and second palladium complex compounds is not particularly limited, and may be the same as the phosphine used in the first to fourth methods. Therefore, all the above descriptions of the phosphine used in the first to fourth methods is applicable to that of the novel first and second palladium complex compounds.

Each of the novel first and second palladium complex compounds can be crystalline, can be dissolved in various organic solvents, thereby becoming stable. Furthermore, these compounds are each stable in the air at room temperature. Due to such physical and chemical properties of these compounds, it becomes easy to isolate these compounds, thereby making them high in purity. Furthermore, it is easy to store these compounds, thereby making them easy to be handled in an industrial scale use. Each of the novel first and second palladium complex compounds has catalytic activity in various reactions, such as (1) carbonylation of an aromatic compound through an insertion of monoxide or the like into a halogenated aryl and the subsequent reductive release, (2) vinylation through an insertion of olefin into a halogenated aryl and the subsequent reductive release, and (3) coupling of a halogenated aryl. For example, an example of the novel first palladium complex compound, [3,5-bis(trifluoromethyl)benzoato]3',5'-bis(trifluoromethyl)-phenylbis(triphenylphosphine)palladium(II), represented by the following formula, has catalytic activity in vinylation through an insertion of olefin into a halogenated aryl and the subsequent reductive release.

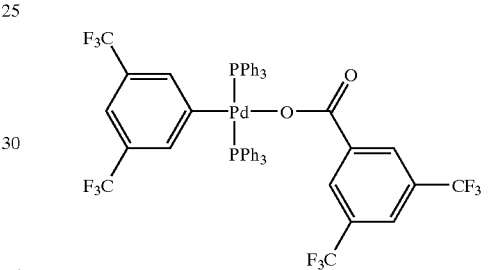

The novel second palladium complex compound may serve as an intermediate for producing a palladium complex compound having different ligands. An example of the novel second palladium complex compound, bromo[3,5-bis(trifluoromethyl) phenyl]bis(triphenylphosphine)palladium(II), represented by the following formula, has catalytic activity in the above-mentioned carbonylation, vinylation, coupling, and the like.

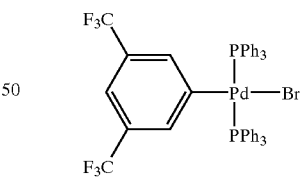

The novel second palladium complex compound can be used as catalyst (Cat. Pd) in a reaction represented by the following reaction formula:

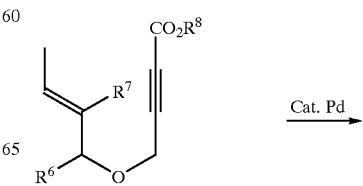

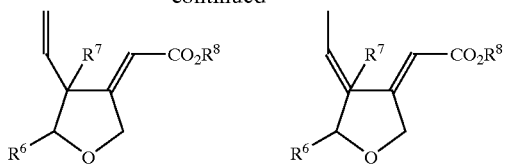

wherein each of $R^6$, $R^7$ and $R^8$ is independently an inert functional group. Examples of such inert functional group are alkyl groups of $C_1$–$C_8$, such as methyl, ethyl, isopropyl, n-butyl, t-butyl, and diisopropylmethyl. This reaction can be conducted by using a solvent, such as methanol, ethanol, isopropanol, benzene, toluene, ethyl acetate, THF, methylene chloride, 1,2-dichloroethane, or acetone. The amount of the novel second palladium compound is preferably of about 0.01–20 mol %, more preferably of about 0.05–10 mol %, based on the number of moles of the substrate. Furthermore, the reaction may be conducted for about 10–100 hr at a temperature of about 10–100° C., preferably about 20–70° C., to complete the reaction. These conditions of the reaction may be modified depending on the amount(s) of the reactant (s).

The following nonlimitative examples are illustrative of the present invention. The pressure is expressed in gauze pressure, unless otherwise stated.

EXAMPLE 1

Synthesis of Bromo[3,5-bis(trifluoromethyl)phenyl]bis(triphenylphosphine)palladium(II)

A stainless steel autoclave was charged with 32.5 g of 3,5-bis(trifluoromethyl)bromobenzene, 25.0 g of palladium acetate, 87.3 g of triphenylphosphine, and 75 ml of tetrahydrofuran, followed by stirring. Then, the autoclave was further charged with 38.0 g of 25% aqueous ammonia. Then, the atmosphere of the autoclave was replaced with nitrogen two times. Then, the nitrogen pressure was adjusted to 3 kg/cm², and it was started to stir the mixture. With this, the inside temperature of the autoclave has increased. Then, it was started to heat the autoclave by adjusting an oil bath temperature to 105° C. About 1.8 hr later, the inside temperature has reached 97° C., and the oil bath was removed. Then, the autoclave was cooled down in order to stop the reaction. Then, 200 ml of toluene was added to the reaction liquid, followed by stirring for several minutes. The thus treated liquid was subjected to a vacuum filtration. Then, the obtained solid matter was washed with a small amount of n-hexane and then dried, thereby obtaining 72.1 g of pale green crystals. Then, the crystals were subjected to recrystallization using methylene chloride, thereby obtaining 48.7 g of crystals. The crystals were identified as being bromo [3,5-bis(trifluoromethyl)phenyl]bis(triphenylphosphine)palladium(II) by the following properties: melting point: (decomposition at a temperature of not lower than 192° C.);

IR (KBr:cm-1):3052, 1435, 1443, 1166, 1095, 749, 693, and 517;

$^1$H-NMR:(standard substance: TMS, solvent: $CDCl_3$):

δ ppm 6.75(s,1H), 7.09 (s,2H), 7.24–7.37(m,18H), and 7.50–7.55(m,12H); and $^{31}$P-NMR: (standard substance: 85% $H_3PO_4$, solvent: $CDCl_3$) δ ppm 27.33(s).

EXAMPLE 2

Synthesis of Iodo[3,5-bis(trifluoromethyl)phenyl]bis(triphenylphosphine)palladium(II)

In this example, Example 1 was repeated except in that the autoclave was charged with 4.00 g of 3,5-bis(trifluoromethyl)iodobenzene, 2.64 g of palladium acetate, 9.29 g of triphenylphosphine, 8.91 g of tetrahydrofuran, and 3.45 g of aqueous ammonia and that the reaction was conducted under a condition that the reaction temperature was in a range of 60–80° C. and the reaction time was 3 hr. With this, there was obtained 8.81 g of crystals. The crystals were identified as being iodo[3,5-bis(trifluoromethyl)phenyl]bis(triphenylphosphine)palladium(II) by the following properties: melting point: (decomposition at a temperature of not lower than 170° C.)

$^1$H-NMR:(standard substance: TMS, solvent: $CDCl_3$):

δ ppm 6.75(s,1H), 7.07(s,2H), 7.24–7.37(m,18H), and 7.48–7.56(m,12H).

REFERENTIAL EXAMPLE 1

Synthesis of 3,5-bis(trifluoromethyl)benzoic acid

A stainless steel autoclave was charged with 400 g of 3,5-bis(trifluoromethyl)bromobenzene, 2.40 g of bromo[3,5-bis(trifluoromethyl)phenyl]bis(triphenylphosphine)palladium(II), followed by mixing. Then, the autoclave was further charged with 291.4 g of triethylamine, 0.887 g of triphenylphosphine, and 200 g of water. While the autoclave was closed, it was started to stir the mixture. Then, the atmosphere of the autoclave was replaced with nitrogen three times and then with carbon monoxide three times. The initial pressure of carbon monoxide was adjusted to 3 kg/cm², and it was started to heat the autoclave in an oil bath. When the inside temperature reached 104–105° C., the inside pressure was adjusted to 8.5 kg/cm². Then, the autoclave was maintained at an inside temperature of 105° C. and an inside pressure of 8.5 kg/cm², while the amount of carbon monoxide to be introduced was adjusted. About 16 hr later, the heating was stopped, and then the autoclave was cooled down. Then, the inside gas was purged. The reaction liquid was put into a separating funnel, followed by the addition of 200 ml of water. The thus treated liquid was dropped by a dropping funnel to 370 g of a 6N—HCl aqueous solution contained in a 2-liter beaker, while this solution was maintained at a temperature of 20–30° C. and stirred. With this, crystals were precipitated, then separated by vacuum filtration, and then washed with 1120 ml of water and then 336 ml of cooled toluene, thereby obtaining 279 g of colorless crystals of 3,5-bis(trifluoromethyl)benzoic acid.

EXAMPLE 3

Synthesis of Trans-[3,5-bis(trifluoromethyl)benzoato]3',5'-bis (trifluoromethyl)phenylbis(triphenylphosphine)palladium(II)

At first, Example 1 was repeated except that the recrystallization was omitted, thereby obtaining pale green crystals of bromo[3,5-bis(trifluoromethyl)phenyl]bis(triphenylphosphine)palladium (II). Then, a stainless steel autoclave was charged with 70.0 g of the obtained bromo[3,5-bis(trifluoromethyl)phenyl]bis(triphenylphosphine)palladium (II), 39.1 g of 3,5-bis(trifluoromethyl)benzoic acid, and 150 ml of tetrahydrofuran, followed by mixing and stirring. The autoclave was further charged with 20.5 g of 25% aqueous ammonia. Then, the atmosphere of the autoclave was replaced with nitrogen two times. Then, the nitrogen pressure was adjusted to 3 kg/cm², and it was started to stir the mixture. Then, it was started to heat the autoclave by adjusting an oil bath temperature to 100° C. About 2 hr later, the oil bath was removed. Then, the autoclave was cooled down. Then, 500 ml of toluene and 200 ml of 25% aqueous ammonia were added to the reaction liquid, followed by stirring for several minutes. Then, an upper organic layer (toluene layer) was washed with water two times and then with a saturated brine, then dried with anhydrous magnesium sulfate, and then concentrated by distilling volatile matters off, thereby obtaining 75.3 g of pale yellow crystals. The crystals were identified as being trans-[3,5-bis(trifluoromethyl)benzoato]3', 5'-bis (trifluoromethyl)phenylbis(triphenylphosphine)palladium (II) by the following properties:

melting point: 168–170° C. (decomposition);

IR (Kr:cm−1): 3060, 2926, 1637, 1437, 1321, 1277, 1173, 1127, 748, 697, and 518;

$^1$H-NMR:(standard substance: TMS, solvent: CDCl$_3$):

δ ppm 6.97(s,1H), 7.09(s,2H), 7.20–7.32(m,18H), 7.40–7.50(m,12H), 7.53(s,2H), and 7.62(s,1H); and $^{31}$P-NMR: (standard substance: 85% H$_3$PO$_4$, solvent: CDCl$_3$): δ ppm 25.73(s).

EXAMPLE 4

Synthesis of [3,5 bis(trifluoromethyl)benzoato]3', 5'-bis trifluoromethyl)phenylbis(triphenylphosphine) palladium(II)

A stainless steel autoclave was charged with 65.3 g of 3,5 -bis(trifluoromethyl)bromobenzene, 100 ml of tetrahydrofuran, 50.0 g of palladium acetate, 175.5 g of triphenylphosphine, 57.6 g of 3,5-bis(trifluoromethyl) benzoic acid, and 60.8 g of 25% aqueous ammonia. Then, the atmosphere of the autoclave was replaced with nitrogen two times. Then, the nitrogen pressure was adjusted to 3 kg/cm$^2$, and it was started to stir the mixture. With this, the inside temperature of the autoclave has increased to about 50° C. Then, it was started to heat the autoclave by adjusting an oil bath temperature to 120° C. About 2 hr later, the inside temperature has reached 95.6° C., and the oil bath was removed. Then, the autoclave was cooled down. Then, 200 ml of water and 600 ml of toluene were added to the reaction liquid, followed by stirring for several minutes. The thus treated liquid was subjected to a vacuum filtration. An organic layer (upper layer) of the obtained filtrate was washed two times with a saturated brine, then dried with anhydrous magnesium sulfate, and then concentrated by distilling volatile matters off. Solid matter precipitated at the initial stage of this concentration was separated by filtration. Furthermore, the filtrate was concentrated, and then n-hexane was added thereto, followed by cooling. Then, the precipitated solid matter was separated by filtration, thereby obtaining 187.5 g of a crude product. This crude product was subjected to recrystallization using toluene, thereby obtaining 143.0 g of pale yellow crystals, The crystals were identified as being [3,5-bis(trifluoromethyl)benzoato]3', 5'-bis(trifluoromethyl) phenylbis(triphenylphosphine) palladium(II) by the following properties:

melting point: 168–170° C. (decomposition);

IR (KBr:cm−1): 3060, 2926, 1637, 1437, 1321, 1277, 1173, 1127, 748, 697, and 518;

$^1$H-NMR:(standard substance: TMS, solvent: CDCl$_3$):

δ ppm 6.97(s,1H), 7.09(s,2H), 7.20–7.32(m,18H), 7.40–7.50 (m,12H), 7.53 (s,2H), and 7.62 (s,1H); and $^{31}$P-NMR: (standard substance: 85% H$_3$PO$_4$, solvent: CDCl$_3$): δ ppm 25.73(s).

EXAMPLE 5

Synthesis of [3,5-bis(trifluoromethyl)benzoato]3'--trifluoromethylphenylbis(triphenylphosphine) palladium(II)

A stainless steel autoclave was charged with 25.0 g of 3-trifluoromethylbromobenzene, 75 ml of tetrahydrofuran, 25 g of palladium acetate, 87.3 g of triphenylphosphine, 38 g of 25% aqueous ammonia, and 57.5 g of 3,5-bis (trifluoromethyl)benzoic acid. Then, the same procedures of Example 4 were repeated, thereby obtaining 32.3 g of a reaction product. This reaction product was identified as being [3,5-bis(trifluoromethyl)benzoato]3'-trifluoromethylphenyl bis(triphenylphosphine)palladium(II) by the following properties:

$^1$H-NMR:(standard substance: TMS, solvent: CDCl$_3$):

δ ppm 6.47(dd, J=7.3, 7.8 Hz, 1H), 6.77(d, J=7.3 Hz, 1H), 6.80(brs, 1H), 6.95(d, J=7.8 Hz, 1H), 7.24–7.30(m, 18H), and 7.40–7.46(m, 12H).

REFERENTIAL EXAMPLE 2

Synthesis of 3,5-bis(trifluoromethyl)cinnamic acid n-butyl ester

At first, 9.02 g of a vacuum-dried anhydrous sodium acetate was put into a 200 ml flask. Under nitrogen stream, 29.3 g of 3,5-bis(trifluoromethyl)bromobenzene, 15.4 g of n-butyl acrylate, 210 mg of [3,5-bis(trifluoromethyl) benzoato]3',5'-bis(trifluoromethyl)phenylbis (triphenylphosphine)palladium(II) (the palladium complex compound prepared in Example 4), and 70 ml of N,N-dimethylacetamide. Then, the flask was heated in an oil bath with stirring. After conducting the reaction for about 1 hr at 110° C., the reaction liquid was cooled down to room temperature. Then, the reaction liquid was poured into an iced water. Organic matter of the reaction liquid was extracted by ether. The obtained organic layer (ether layer) was separated from the aqueous layer, then washed with water three times and then with a saturated brine two times, and then dried with anhydrous magnesium sulfate. Then, the solvent was distilled off under vacuum using an evaporator, thereby obtaining a brown solid matter as residue. This solid matter was subjected to recrystallization using n-hexane, thereby obtaining 22.3 g of crystals. The crystals were identified as being 3,5-bis(trifluoromethyl) cinnamic acid n-butyl ester by the following properties:

melting point: 47–48° C. (decomposition); and $^1$ H-NMR:(standard substance: TMS, solvent: CDCl$_3$):

δ ppm 0.975(t, J=7.3 Hz, 3H), 1.38–1.50(m, 2H), 1.66–1.76(m, 2H), 4.25(t, J=6.6 Hz, 2H), 6.57(d, J=16 Hz, 1H), 7.70(d, J=16 Hz, 1H), 7.86(s, 1H), and 7.93(s, 2H).

EXAMPLE 6

A 100 ml pressure-tight reaction tube replaced with argon was charged with 204 mg (0.91 mmol) of palladium acetate, 1.28 g (2.72 mmol) of (S)-2-methoxy-2'-(diphenylphosphino)-1,1'-binaphthyl[(S)—MeO—MOP], 266 mg (0.91 mmol) of 3,5-bis(trifluoromethyl) bromobenzene, and 1 ml of tetrahydrofuran, followed by mixing and stirring. Then, 0.5 ml of 28% aqueous ammonia was added thereto, and then the atmosphere of the reaction tube was replaced again with argon. After that, the reaction tube was tightly closed without adding pressure thereto. Then, the reaction tube was heated for 6 hr in an oil bath of 110° C., followed by cooling down to room temperature. Then, 1 ml of pure water and 3 ml of toluene were added to the reaction liquid, followed by stirring for several minutes. The thus treated liquid was subjected to a vacuum filtration. The obtained filtrate was washed with a saturated brine two times, then dried with anhydrous magnesium sulfate, and then concentrated, thereby obtaining a mixture in the form of a brown syrup. The obtained mixture was subjected to a thin-layer chromatography using a neutral silica gel column (methylene chloride:hexane 1:1). With this, a product having a Rf value of 0.50 (hexane:ethyl acetate=2:1) was obtained with a yield of 22.1%. This product was identified as a palladium complex compound [MBT—Pd—Br((S)—MeO—MOP) having the following formula, by the following properties:

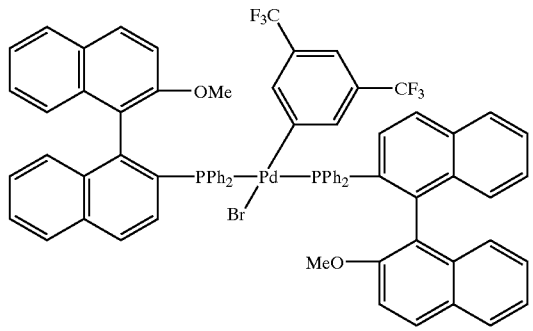

¹H-NMR: (300 MHz, standard substance: TMS, solvent: CDCl₃):

δ ppm: 3.35(s, 6H), 6.48–6.63(m, 9H), 6.65–6.80(m, 10H), 6.85–6.95 (m, 4H), 7.04–7.16(m, 10H), 7.27 (bs, 1H), 7.50–7.60(m, 7H), 7.95(d, 2 H, J=8.1 Hz), 8.05(d, 2 H, J=8.7 Hz), and 8.84–8.95 (m, 2H); and IR (KBr powder: cm⁻¹): 3060, 1626, 1595, 1512, 1435, 1342, 1276, 1258, 1178, 1127, 1087, 878, 806, 745, and 690.

The procedures for obtaining the above palladium complex compound were repeated except in that (S)—MeO—MOP was replaced with (R)-2-methoxy-2-(diphenylphosphino)-1,1'-binaphthyl [(R)—MeO—MOP], thereby obtaining another palladium complex compound [MBT—Pd—Br((R)—MeO—MOP)] that is a stereoisomer (R-configuration) of the above palladium complex compound.

EXAMPLE 7

A 100 ml pressure-tight reaction tube replaced with argon was charged with 449 mg (2 mmol) of palladium acetate, 1.83 g (3 mmol) of (R)-2,2'-bis(diphenylphosphino)-1,1'-binaphthyl[(R)-BINAP], 586 mg (3 mmol) of 3,5-bis(trifluoromethyl)bromobenzene, and 2 ml of tetrahydrofuran, followed by mixing and stirring. Then, 1 ml of 28% aqueous ammonia was added thereto, and then the atmosphere of the reaction tube was replaced again with argon. After that, the reaction tube was tightly closed without adding pressure thereto. Then, the reaction tube was heated for 6 hr in an oil bath of 110° C. Then, the reaction tube was cooled down to room temperature. Then, 2 ml of pure water and 6 ml of toluene were added to the reaction liquid, followed by stirring for several minutes. The thus treated liquid was subjected to a vacuum filtration. The obtained filtrate was washed with a saturated brine two times, then dried with anhydrous magnesium sulfate, and then concentrated, thereby obtaining a mixture in the form of a brown syrup. The obtained mixture was subjected to a thin-layer chromatography using a neutral silica gel column (methylene chloride:hexane=2:1). With this, a product having a Rf value of 0.38 (hexane:ethyl acetate=2:1) was obtained with a yield of 38.2%. This product was identified as a palladium complex compound [MBT—Pd—Br((R)-BINAP) having the following formula, by the following properties:

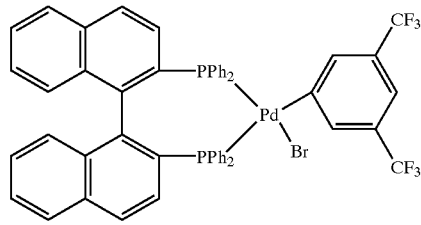

¹H-NMR: (300 MHz, standard substance; TMS, solvent: CDCl₃):

δ ppm: 6.58–6.82 (m, 8H), 6.96–7.16(m, 9H), 7.33 (d, 1 H, 7.5 Hz), 7.38(d, 1 H, 6.3 Hz), 7.40–7.64(m, 10H), 7.69(dd, 1 H, J=9.0, 1.8 Hz), and 7.76–7.94(m, 5H);

³¹P-NMR: (376 MHz, solvent: CDCl₃):

δ ppm 14.84(d, J=38.1) and 30.51(d, J=40.0);

¹⁹F-NMR: (376 MHz, standard substance: BTF, solvent: C₆D₃):

δ ppm-62.98(s); and

IR (KBr powder: cm⁻¹): 3060, 1607, 1586, 1572, 1657, 1502, 1483, 1437, 1342, 1311, 1276, 1226, 1176, 1098, 1027, 1000, 880, 837, 816, 743, and 692.

EXAMPLE 8

An argon-replaced Pyrex tube equipped with a screw stopper was charged with 40.0 mg (0.03 mol) of the palladium complex compound [MBT—Pd—Br((R)—MeO—MOP)] prepared in Example 6 and 100.9 mg (0.6 mmol) of 4-(2-butenyloxy)-butynoic acid methyl ester and 1.5 ml of benzene, followed by stirring for about 3 minutes at room temperature. After dissolving the palladium complex compound, 6.9 mg (0.03 mol) of silver benzoate was added thereto. Then, the atmosphere of the tube was replaced again with argon. After that, the tube was tightly closed, followed by stirring in an oil bath of 60° C. for 1.5 hr. After confirming the termination of the reaction by a thin-layer chromatography, the reaction solution was concentrated. Then, a product was isolated using a silica gel column with a development solvent (hexane:ethyl acetate=50:1), The conversion was 100%. The isolated product was a combination of 1,4-diene (b) and 1,3-diene (c) represented by the following formulas, and the ratio of (b)/(c) was found to be 79/21 by ¹ H-NMR.

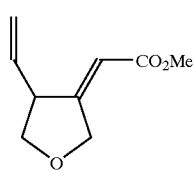

(b)

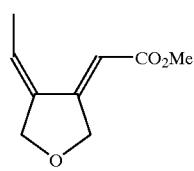

(c)

EXAMPLE 9

In this example, Example 8 was repeated except in that 6.9 mg (0.03 mol) of silver benzoate was replaced with 6.6 mg (0.03 mol) of silver trifluoroacetate. The conversion was 100%. The isolated product was a combination of 1,4-diene (b) and 1,3-diene (c) represented by the above formulas, and the ratio of (b)/(c) was found to be 76/24 by $^1$H-NMR.

EXAMPLE 10

An argon-replaced Pyrex tube equipped with a screw stopper was charged with 40.0 mg (0.03 mol) of the palladium complex compound [MBT—Pd—Br((R)—MeO—MOP)] prepared in Example 6 and 100.9 mg (0.6 mmol) of 4-(2-butenyloxy)-butynoic acid methyl ester and 1.5 ml of benzene. Then, the tube was tightly closed, followed by stirring for about 3 minutes at room temperature. After dissolving the palladium complex compound, the mixture was stirred in an oil bath of 60° C. for 5 hr. After confirming the termination of the reaction by a thin-layer chromatography, the reaction solution was concentrated. Then, the product was isolated using a silica gel column with a development solvent (hexane:ethyl acetate=50:1). The conversion was 48%. The isolated product was a combination of 1,4-diene (b) and 1,3-diene (c) represented by the above formulas, and the ratio of (b)/(c) was found to be 82/18 by $^1$H-NMR.

EXAMPLE 11

An argon-replaced Pyrex tube equipped with a screw stopper was charged with 40.0 mg (0.03 mol) of the palladium complex compound [MBT—Pd—Br((R)—MeO—MOP)] prepared in Example 6 and 109.2 mg (0.6 mmol) of 4-(2-methyl-2-butenyloxy)-butynoic acid methyl ester and 1.0 ml of benzene-$d_6$, followed by stirring for about 3 minutes at room temperature. After dissolving the palladium complex compound, 6.6 mg (0.03 mmol) of silver trifluoroacetate was added thereto. Then, the atmosphere of the tube was replaced again with argon, After that, the tube was tightly closed, followed by stirring in an oil bath of 60° C. for 24 hr. After confirming the termination of the reaction by a thin-layer chromatography, the reaction solution was concentrated. Then, a product having the following formula was isolated using a silica gel column with a development solvent (hexane: ethyl acetate=50:1).

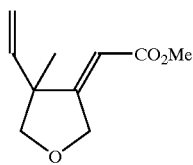

(b)

The yield of the obtained 1,4-diene was 100%, and its ee yield (enantio-selectivity) was 3%.

EXAMPLE 12

An argon-replaced Pyrex tube equipped with a screw stopper was charged with 30.7 mg (0.03 mmol) of the palladium complex compound [MBT—Pd—Br((R) BINAP)] prepared in Example 7, 109.2 mg (0.6 mmol) of 4-(2-methyl-2-butenyloxy)-butynoic acid methyl ester and 1.0 ml of benzene-$d_6$, followed by stirring for about 3 minutes at room temperature. After dissolving the palladium complex compound, 6.6 mg (0.03 mmol) of silver trifluoroacetate was added thereto. Then, the atmosphere of the tube was replaced again with argon. After that, the tube was tightly closed, followed by stirring in an oil bath of 60° C. for 24 hr. After confirming the termination of the reaction by a thin-layer chromatography, the reaction solution was concentrated. Then, a product represented by the formula shown in Example 11 was isolated using a silica gel column with a development solvent (hexane:ethyl acetate=50:1). The yield of the obtained 1,4-diene was 14%, and its ee yield (enantio selectivity) was 84%.

REFERENTIAL EXAMPLE 3

An argon-replaced Pyrex tube equipped with a screw stopper was charged with 6.7 mg (0.03 mmol) of $Pd(OAc)_2$, 156.6 mg (0.03 mmol) of (R)-BINAP, 109.2 mg (0.6 mmol) of 4-(2-methyl-2-butenyloxy)-butynoic acid methyl ester, and 1.0 ml of benzene, followed by stirring for about 3 minutes at room temperature. After dissolving the palladium complex compound, the atmosphere of the tube was replaced again with argon. After that, the tube was tightly closed, followed by stirring in an oil bath of 60° C. for 8 hr. After confirming the termination of the reaction by a thin-layer chromatography, the reaction solution was concentrated. Then, a product represented by the formula shown in Example 11 was isolated using a silica gel column with a development solvent (hexane:ethyl acetate=50:1). The yield of the obtained 1,4-diene was 100%, and its ee yield (enantio selectivity) was 6%.

The entire disclosure of each of Japanese Patent Application Nos. 10–351529 filed on Dec. 10, 1998, 10-351530 filed on Dec. 10, 1998, 11-78393 filed on Jun. 24, 1999, 11-178394 filed on Jun. 24, 1999, 11-178395 filed on Jun. 24, 1999, and 11-329084 filed on Nov. 19, 1999, including specification, claims, and summary, is incorporated herein by reference in its entirety.

What is claimed is:

1. A method for producing a palladium-complex compound represented by formula (2),

$Ar^1$-$PdL_2X$         (2)

where $Ar^1$ is an aryl group represented by formula (6);

(6)

where $R^2$ is a trifluoromethyl group, and m is an integer 4 from 2 to 4, each L is independently a phosphine ligand, and two of L are optionally bonded together to form a diphosphine, and X is a halogen that is fluorine, chlorine, bromine or iodine, trifluoromethanesulfonate group, an alkylsulfonate group having a carbon atom number of 1–4, or a substituted or unsubstituted arylsulfonate group, said method comprising:

reacting an aromatic compound represented by formula (1),

$Ar^1X$         (1)

where $Ar^1$ and X are defined as above, with a palladium compound and a phosphine derivative, in the presence of a basic substance, thereby obtaining said palladium-complex compound, $Ar^1$-$PdL_2X$.

2. A palladium complex compound represented by the formula $Ar^5$-$PdL_2X$ where $Ar^5$ is bis(trifluoromethyl)phenyl group, X is a halogen that is fluorine, chlorine, bromine or iodine, each L is independently a phosphine ligand, and two of L are optionally bonded together to form a diphosphine.

3. A method according to claim 1, wherein said aromatic compound is 3,5-bis(trifluoromethyl)bromobenzene or 3,5-bis(trifluoromethyl)iodobenzene.

4. A method according to claim 1, wherein said X in formula (1) is bromine or iodine.

5. A method according to claim 1, wherein said palladium compound is a palladium salt.

6. A method according to claim 1, wherein said phosphine derivative is represented by the formula:

P(R$^1$)$_3$ where each R$^1$ is independently selected from the group consisting of lower alkyl groups, cycloalkyl groups, phenyl group, naphthyl group, anthryl group, pyridyl group and quinolyl group, each R$^1$ optionally having a first substituent R$^2$ selected from the group consisting of nitro group, primary amino group, secondary amino group, tertiary amino group, halogen atoms, and a second substituent, said second substituent being selected from the group consisting of lower alkyl groups, cycloalkyl groups, phenyl group, naphthyl group, anthryl group, pyridyl group and quinolyl group, said second substituent optionally having a third substituent R$^3$ selected from the group consisting of nitro group, primary amino group, secondary amino group, tertiary amino group, halogen atoms, and a substituent being selected from the group consisting of lower alkyl groups, lower alkoxy groups, cycloalkyl groups, phenyl group, naphthyl group, anthryl group, pyridyl group, and quinolyl group, said substituent optionally having a substituent.

7. A method according to claim 6, wherein at least one of said R$^1$ of said phosphine derivative is selected from the group consisting of phenyl group, o-tolyl group, m-tolyl group, p-tolyl group, and 3,5-xylyl group.

8. A method according to claim 6, wherein said phosphine derivative is represented by the following formula:

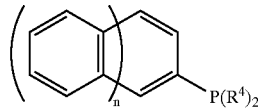

where one or more hydrogen atoms of the naphthalene ring are optionally replaced with said first substituent R$^2$, and each R$^4$ is independently a group selected from the group consisting of phenyl group, o-tolyl group, m-tolyl group, p-tolyl group, and 3,5-xylyl group.

9. A method according to claim 1, wherein said phosphine derivative is represented by the formula (R$^1$)$_2$P-Q-P(R$^1$)$_2$ where Q is a bivalent group, and each R$^1$ is independently selected from the group consisting of lower alkyl groups, cycloalkyl groups, phenyl group, naphthyl group, anthryl group, pyridyl group and quinolyl group, each R$^1$ optionally having a first substituent R$^2$ selected from the group consisting of nitro group, primary amino group, secondary amino group, tertiary amino group, halogen atoms, and a second substituent, said second substituent being selected from the group consisting of lower alkyl groups, cycloalkyl groups, phenyl group, naphthyl group, anthryl group, pyridyl group and quinolyl group, said second substituent optionally having a third substituent R$^3$ selected from the group consisting of nitro group, primary amino group, secondary amino group, tertiary amino group, halogen atoms, and a substituent being selected from the group consisting of lower alkyl groups, lower alkoxy groups, cycloalkyl groups, phenyl group, naphthyl group, anthryl group, pyridyl group, and quinolyl group, said substituent optionally having a substituent.

10. A method according to claim 9, wherein said bivalent group Q comprises at least one of (1) one or more of a first bivalent group selected from the group consisting of alkylene group, phenylene group, naphthylene group, and anthrylene group, and (2) one or more of a bonding group selected from the group consisting of single bond, —O—, —S—, —C(=O)—, and —S(=O)—, said first bivalent group optionally having one or more substituents selected from the group consisting of nitro group, primary amino group, secondary amino group, tertiary amino group, halogen atoms, lower alkyl groups, lower alkoxy groups, cycloalkyl groups, phenyl group, naphthyl group, anthryl group, pyridyl group, and quinolyl group.

11. A method according to claim 9, wherein said bivalent group Q is selected from the group consisting of alkylene group, biphenylene group, binaphthylene group and bianthrylene group, said bivalent group Q being optionally substituted by one or more substituents selected from the group consisting of nitro group, primary amino group, secondary amino group, tertiary amino group, halogen atoms, lower alkyl groups, lower alkoxy groups, cycloalkyl groups, phenyl group, naphthyl group, anthryl group, pyridyl group, and quinolyl group.

12. A method according to claim 1, wherein said phosphine derivative is triphenylphosphine.

13. A method according to claim 1, wherein said basic substance is selected from the group consisting of ammonia and amines.

14. A method according to claim 1, wherein reacting said aromatic compound is conducted in the presence of a solvent.

15. A method according to claim 1, wherein reacting said aromatic compound is conducted in the presence of water as a solvent.

16. A method according to claim 1, wherein reacting said aromatic compound is conducted in a single reaction vessel.

17. A palladium complex compound according to claim 2, wherein said Ar$^5$ is 3,5-bis(trifluoromethyl)phenyl group.

18. A palladium complex compound according to claim 2, wherein each L is represented by the formula:

P(R$^1$)$_3$ where each R$^1$ is independently selected from the group consisting of lower alkyl groups, cycloalkyl groups, phenyl group, naphthyl group, anthryl group, pyridyl group and quinolyl group, each R$^1$ optionally having a first substituent R$^2$ selected from the group consisting of nitro group, primary amino group, secondary amino group, tertiary amino group, halogen atoms, and a second substituent, said second substituent being selected from the group consisting of lower alkyl groups, cycloalkyl groups, phenyl group, naphthyl group, anthryl group, pyridyl group and quinolyl group, said second substituent optionally having a third substituent R$^3$ selected from the group consisting of nitro group, primary amino group, secondary amino group, tertiary amino group, halogen atoms, and a substituent being selected from the group consisting of lower alkyl groups, lower alkoxy groups, cycloalkyl groups, phenyl group, naphthyl group, anthryl group, pyridyl group, and quinolyl group, said substituent optionally having a substituent.

19. A palladium complex compound according to claim 18, wherein at least one of said R$^1$ of each L is selected from the group consisting of phenyl group, o-tolyl group, m-tolyl group, p-tolyl group, and 3,5-xylyl group.

20. A palladium complex compound according to claim 18, wherein each L is represented by the following formula:

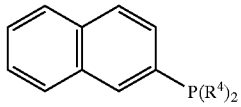

where one or more hydrogen atoms of the naphthalene ring are optionally replaced with said first substituent $R^2$, and each $R^4$ is independently a group selected from the group consisting of phenyl group, o-tolyl group, m-tolyl group, p-tolyl group, and 3,5-xylyl group.

21. A method according claim 1, wherein each L is represented by the formula $(R^1)_2P$-Q-$P(R^1)_2$ where Q is a bivalent group, and each $R^1$ is independently selected from the group consisting of lower alkyl groups, cycloalkyl groups, phenyl group, naphthyl group, anthryl group, pyridyl group and quinolyl group, each $R^1$ optionally having a first substituent $R^2$ selected from the group consisting of nitro group, primary amino group, secondary amino group, tertiary amino group, halogen atoms, and a second substituent, said second substituent being selected from the group consisting of lower alkyl groups, cycloalkyl groups, phenyl group, naphthyl group, anthryl group, pyridyl group and quinolyl group, said second substituent optionally having a third substituent $R^3$ selected from the group consisting of nitro group, primary amino group, secondary amino group, tertiary amino group, halogen atoms, and a substituent being selected from the group consisting of lower alkyl groups, lower alkoxy groups, cycloalkyl groups, phenyl group, naphthyl group, anthryl group, pyridyl group, and quinolyl group, said substituent optionally having a substituent.

22. A method according to claim 21, wherein said bivalent group Q comprises at least one of (1) one or more of a first bivalent group selected from the group consisting of alkylene group, phenylene group, naphthylene group, and anthrylene group, and (2) one or more of a bonding group selected from the group consisting of single bond, —O—, —S—, —C(=O)—, and —S(=O)—, said first bivalent group optionally having one or more of a substituent selected from the group consisting of nitro group, primary amino group, secondary amino group, tertiary amino group, halogen atoms, lower alkyl groups, lower alkoxy groups, cycloalkyl groups, phenyl group, naphthyl group, anthryl group, pyridyl group, and quinolyl group.

23. A method according to claim 21, wherein said bivalent group Q is selected from the group consisting of alkylene group, biphenylene group, binaphthylene group and bianthrylene group, said bivalent group Q being optionally substituted by one or more substituents selected from the group consisting of nitro group, primary amino group, secondary amino group, tertiary amino group, halogen atoms, lower alkyl groups, lower alkoxy groups, cycloalkyl groups, phenyl group, naphthyl group, anthryl group, pyridyl group, and quinolyl group.

24. A palladium complex compound according to claim 2, wherein each L is triphenylphosphine.

25. A palladium complex compound represented by formula (8),

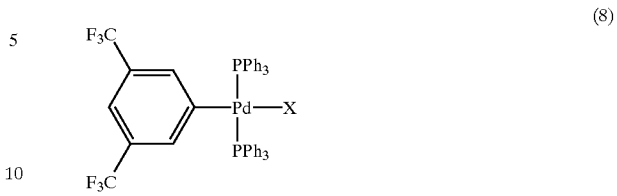

where Ph is phenyl group, X is a halogen that is fluorine, chlorine, bromine or iodine.

26. A palladium complex compound represented by formula (9),

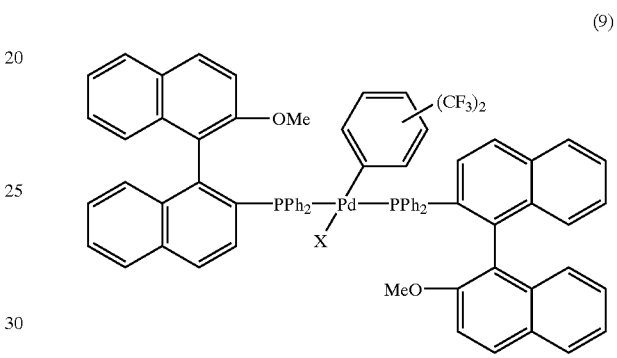

where X is a halogen that is fluorine, chlorine, bromine or iodine, trifluoromethanesulfonate group, an alkylsulfonate group having a carbon atom number of 1–4, or substituted or unsubstituted arylsulfonate group.

27. A palladium complex compound represented by formula (10)

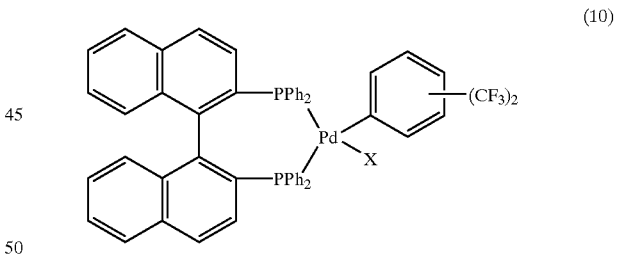

where X is a halogen that is fluorine, chlorine, bromine or iodine, trifluoromethanesulfonate group, an alkylsulfonate group having a carbon atom number of 1–4, or substituted or unsubstituted arylsulfonate group.

* * * * *